United States Patent [19]
Cano

[11] Patent Number: 5,341,811
[45] Date of Patent: Aug. 30, 1994

[54] METHOD AND APPARATUS FOR OBSERVATION OF VENTRICULAR LATE POTENTIALS

[75] Inventor: Gerald G. Cano, Pittsburgh, Pa.

[73] Assignee: Allegheny-Singer Research Institute, Pittsburgh, Pa.

[21] Appl. No.: 675,996

[22] Filed: Mar. 26, 1991

[51] Int. Cl.$^5$ ............................................ A61B 5/0452
[52] U.S. Cl. ................................. 128/696; 364/413.06
[58] Field of Search ............... 128/696, 901, 702, 708; 364/413.06, 413.05

[56] References Cited

U.S. PATENT DOCUMENTS

| | | | |
|---|---|---|---|
| 4,038,536 | 7/1977 | Feintuch | 128/698 |
| 4,422,459 | 12/1983 | Simson | 128/702 |
| 4,458,691 | 7/1984 | Netravali | 128/705 |
| 4,458,692 | 7/1984 | Simson | 128/705 |
| 4,492,235 | 1/1985 | Sitrick | 128/705 |
| 4,630,204 | 12/1986 | Mortara | 364/417 |
| 4,751,931 | 6/1988 | Briller et al. | 128/700 |
| 4,781,201 | 11/1988 | Wright | 128/696 |
| 4,793,361 | 12/1988 | DuFault | 128/696 |
| 4,802,222 | 1/1989 | Weaver | 128/696 |
| 4,991,587 | 2/1991 | Blakeley et al. | 128/696 |

OTHER PUBLICATIONS

Cain, M.; Dieter Ambos, Joanne Markham, Albert Fischer, and Burton Sobel;"Quantification of Differences in Frequency Content of Signal-Averaged Electrocardiograms in Patients with Compared to Those Without Sustained Ventricular Tachycardia", American Journal of Cardiology 1985; 55:1500–1505.

Cano, Gerald, Stanley Briller, and Douglas Coast; "Enhancement of Low-Level ECG Components in Noise with Time-Sequenced Adaptive Filtering"; Journal of Electrocardiology, (to be published).

El-Sherif, Nabil; Rahul Mehra, J. A. C. Gomes and George Kelen; "Appraisal of a Low Noise Electrocardiogram", Journal of the American College of Cardiology, 1983.

Ferrara, Earl, R., Jr., and Bernard Widrow, "The Time-Sequenced Adaptive Filter"; Thesis; 1978.

Homback, V.; U. Kebbel, H.-W. Hopp, U. Winter and H. Hirche; "Noninvasive beat-by-beat registration of ventricular late potentials using high resolution electrocardiography"; International Journal of Cardiology, 1984; 6:167.

Shelton, Lynn U.; Gerald Cano, Douglas Coast and Stanley Briller; "Detection of Late Potentials by Adaptive Filtering"; Journal of Electrocardiology (to be published).

Simon, Michael B.; "Use of Signals in the Terminal QRS Complex to Identify Patients with Ventricular Tachycardia After Myocardial Infarction"; Circulation, 1981; 64(2).

Widrow, Bernard; John Glover, John McCool, John Kaunitz, Charles Williams, Robert Hearn, James Zeidler, Eugene Dong and Robert Goodlin; "Adaptive Noise Cancelling: Principles and Applications"; Proceedings of the IEEE, 1975; 63:1692.

Primary Examiner—William E. Kamm
Assistant Examiner—Kennedy J. Schaetzle
Attorney, Agent, or Firm—Webb Ziesenheim Bruening Logsdon Orkin & Hanson

[57] ABSTRACT

The present invention is directed to a method and apparatus for enhancing high resolution ECG signals acquired with electrodes on the surface of a patient's thorax so that ventricular late potentials can be detected and observed. The ECG signals are detected, measured and digitized and are then processed to remove low frequency components and preferably, common mode signals. Enhancement is then accomplished by filtering out the remaining electrical interference caused by underlying muscle tissue, nerve tissue and environmental noise with a particular adaptive filtering technique.

42 Claims, 6 Drawing Sheets

METHOD AND APPARATUS FOR OBSERVATION OF VENTRICULAR LATE POTENTIALS

BACKGROUND OF THE INVENTION

1. Field of the Invention

This invention relates to the surface detection of low level bioelectric signals and, more particularly, to the surface detection of ventricular late potentials.

2. Description of the Prior Art

Sudden death following apparent recovery from uncomplicated acute myocardial infarction is not an uncommon event in modern medicine. It is usually ascribed to the unforeseen development of malignant ventricular arrhythmias that do not spontaneously terminate. Ventricular arrhythmias can lead to ventricular tachycardia, a condition in which the heart beats rapidly, pumping only a minimal amount of blood. During attacks of ventricular tachycardia, the patient may collapse due to an inadequate blood supply. Ventricular tachycardia can lead to ventricular fibrillation, a situation in which the heart simply quivers, pumping no blood at all. The patient will die unless immediate medical treatment reestablishes synchronous beating of the heart.

Post myocardial infarction patients who are at risk for sudden death from ventricular arrhythmias may have no indication until a life-threatening event occurs. Those who experience prolonged episodes of ventricular tachycardia have a high mortality rate. Survivors may undergo special invasive electrophysiological testing. Testing involves attempts to induce a ventricular arrhythmia to assess possible susceptibility to future spontaneous development of ventricular arrhythmias. During testing, if sustained, ventricular tachycardia is induced, implying susceptibility, treatment with antiarrhythmics may be initiated followed by further testing for inducibility of arrythmias. Such testing/treatment programs may involve extended hospitalization and trauma.

Within the last twelve years, studies have disclosed that low amplitude high frequency electrical signals called "ventricular late potentials" are often present in the electrocardiograms (ECGs) of patients who, after myocardial infarction, have episodes of potentially dangerous ventricular arrhythmias. Specifically, these ventricular late potentials often follow the terminal portion of the QRS complex or occur during the ST segment, T-wave or other diastolic portions of the ECG. While the precise origin of these waveforms is unknown, it is believed that these ventricular late potentials are generated by small islands of muscle cells located within cardiac scar tissue. These ventricular late potentials can initiate ventricular arrhythmias.

Because ventricular late potentials are very small amplitude electrical signals, they are difficult to observe in standard ECGs acquired with electrodes placed on the patient's thorax. The ventricular late potentials are obscured at the surface of the thorax by the electrical interference or "noise" from intervening nerve and muscle tissue and environmental noise, particularly 60 Hz and its harmonics.

Several attempts have been made in the prior art to measure the analog ECG waveform, convert the waveform to a digital signal and then digitally filter out the noise component in order to isolate, enhance and identify whether ventricular late potentials are present in ECGs measured on the surface of the body.

Simson, "Use of Signals in the Terminal QRS Complex to Identify Patients with Ventricular Tachycardia After Myocardial Infarction", *Circulation* 64:2, 1981, first demonstrated the existence of small, high frequency electrocardiographic potentials in ECGs measured on the surface of the body of post myocardial infarction patients. He digitized and averaged bipolar leads orthogonally oriented along X, Y and Z axes of a cartesian coordinate system of a patient's thorax. Each lead average was digitally filtered. Simson's filter does not reduce either myoelectric artifacts or environmental noise (60 Hz and its harmonics), which are major components that can obscure ventricular late potentials in the ECG.

Nonetheless, Simson reported two useful measures for identifying the presence of ventricular late potentials in the ECG signal: 1) root-mean-squared (RMS) amplitude of the last 40 milliseconds of the QRS complex ($V_{rms40}$); and 2) duration of the QRS complex. Another measure that has come into use is the duration of the interval from offset of the QRS complex back to that point in the QRS complex where its amplitude first exceeds 40 microvolts, an experimentally determined threshold; this is usually termed the low amplitude signal duration (LASD). Ventricular late potentials are low amplitude signals in the tail of the QRS complex. If the RMS amplitude ($V_{rms40}$) of the tail (or last 40 milliseconds) of the QRS complex is found to exceed an experimentally established value, it is assumed that the signal is simply a portion of the tail of the QRS complex itself, not a ventricular late potential. However, if the RMS amplitude falls below the experimentally established value, the signal may be a ventricular late potential.

Measurement of the overall duration of the QRS complex assumes that its duration will increase substantially from the typical average of 100 milliseconds in the presence of a ventricular late potential because the ventricular late potential occurs late in the QRS complex, thus lengthening the overall time or duration of the QRS complex waveform. For the LASD measurement, it is assumed that where there is no ventricular late potential, the interval of time from the end of the QRS complex "backwards" in time into the QRS complex where the QRS complex first exceeds 40 millivolts will be 40 milliseconds or less. If a ventricular late potential is present, this interval of time will increase due to the occurrence of ventricular late potential. Abnormal values for these three measurements indicating the existence of ventricular late potentials are: 1) $V_{rms40}$ equal to or less than 25 microvolts; 2) QRS duration greater than or equal to 120 milliseconds; and 3) LASD equal to or greater than 40 milliseconds.

Cain, et al., "Quantification of Differences in Frequency Content of Signal Averaged Electrocardiograms in Patients with Compared to Patients Without Sustained Ventricular Tachycardia", *American Journal of Cardiology*, 55: 1500, 1985, attempted to differentiate normal bipolar lead signals from those containing late potentials on the basis of frequency content. El-Sherif, et al., "Appraisal of a Low Noise Electrocardiogram", *Journal of the American College of Cardiology*, 1(2):456, 1983, used low-noise techniques and spatial averaging of 16 simultaneously recorded bipolar signals to identify low amplitude, late diastolic potential s beat-to-beat in the ST segment of post myocardial infarction patients with a propensity for development of ventricular arrhythmias. Hombach, et al., "Noninvasive Beat-by-beat Registration of Ventricular Late Potentials Using High Resolution Electrocardiography", *International Journal of Cardiology*, 6:167, 1984, attempted beat-to-beat registration of ventricular late potentials by using spatial averaging of four signals in conjunction with specially designed suction electrodes and low noise preamplifiers. To reduce environmental noise, Hombach, et al. performed the tests inside a Faraday cage, limiting the clinical accessibility to this test.

The use of a technique known as "time-sequenced adaptive filtering" (TSAF) for removing noise from a measured signal has been investigated. Ferrera, "The Time-Sequenced Adaptive Filter", Ph.D. thesis, Stanford University, 1978, first reported on a technique of using TSAF as a refinement of the least-mean-squared-enhancer developed by Widrow, "Stationary and Non-stationary Learning Characteristics of the LMS Adaptive Filter", *Proceedings of the IEEE*, 64:1151, 1976.

Problems associated with the use of the Ferrera algorithm in detecting bioelectric signals (specifically signals generated by the heart's His-Purkinje system) have been investigated. M. T. Juran, "Surface Recordings of His-Purkinje Activity Using Adaptive Filtering", Masters Thesis, Carnegie-Mellon University, 1984, investigated the effects of correlated noise in the input signals to the adaptive filter and devised an adjustment factor to minimize the effects of correlated noise, depending on the degree of correlation.

U.S. Pat. No. 4,751,931, issued Jun. 21, 1988, to Briller, et al., for a "Method and Apparatus for Determining His-Purkinje Activity", developed an improved method and apparatus utilizing TSAF for facilitating observation of His signals in surface ECG signals. Briller, et al. preserves the amplitude and high frequency characteristics of the sharp His signal in a real time data processing apparatus. The device filters out background noise to enhance the His signal in a very short time, typically ten to eleven heart beats, and often preserves beat-to-beat changes. However, Briller, et al. is not suitable for the measurement of ventricular late potentials because it does not provide an accurate estimate of the signal amplitude which is a necessary factor in identifying ventricular late potentials. Further, it would be preferred to have a lower remaining noise after processing in order to identify the weak ventricular late potential signal.

Certain commercially available devices are available for measuring ventricular late potentials. Examples include Predictor SAECG ®, available from Corazonix Corporation and the ART 1200 EPX ™, available from Arrhythmia Research Technology, Inc., of Oklahoma City, Okla. However, these commercial devices are based on Simson's method, typically requiring 200-1000 cardiac cycles to perform analysis and as much as fifteen minutes to acquire enough cycles to identify ventricular late potentials.

SUMMARY OF THE INVENTION

Accordingly, I have developed a method and apparatus which permits the accurate, rapid and non-invasive detection of ventricular late potentials.

At least two ECG signals are acquired from the surface of the body. A first ECG signal is acquired as the difference in electric potential between a first pair of electrodes and a second ECG signal is acquired as the difference in electric potential between a second pair of electrodes. Both ECG signals are bandpass filtered, sampled at sampling points at a constant sampling rate, digitized and stored for processing. The digitized ECG signals are initially processed using a digital high-pass filter algorithm to remove low frequency components of the ECG signal. The high-pass filter algorithm is preferably a four pole, zero phase shift filter algorithm. Common mode signals (60 Hz and/or harmonics) can be reduced in the digitized ECG signals with an adaptive filter using a single least-mean-squared-enhancer for each 60 Hz harmonic.

Using located QRS complexes as reference points, intervals within the ECG waveforms are selected where no ECG activity occurs. Electrical noise is then estimated in each ECG signal using these intervals. The signal with the lesser estimated noise based on the standard deviation in intervals with no signal of several ECG cycles is selected as the "reference" signal. The remaining signal becomes the "input" signal. A portion of the input signal about and containing each QRS complex is then selected and subdivided into filter intervals of equal duration and comprising either a single sample point or several sample points. Each filter interval has its own adaptive filter algorithm which operates only on the same corresponding filter interval in each ECG cycle.

A feedback coefficient associated with each adaptive filter algorithm is computed using the appropriate interval in the input signal. Once computed, these feedback coefficients remain constant during the adaptive filtering process and can be used to compute the initial estimate of bias weight as discussed below and can also be used to control the "convergence" or rate at which the filter adapts to or "learns" the input signal's characteristics.

Bias weights associated with each adaptive filter algorithm are initialized. Each filter interval is then filtered with a time-sequenced adaptive filter algorithm. The characteristics of each adaptive filter algorithm are created in the form of a weight matrix and an added bias weight. The values corresponding to the filtered signal are computed by multiplying the appropriate input signal samples by the corresponding weight matrix and adding the contribution of the bias weight. The adaptation process modifies or updates the weight matrix and bias weight for each interval. These are updated not only in the previous ECG signal but also within the current cycle being filtered, according to an algorithm that reduces the mean-squared-error between the reference signal and the values corresponding to the filtered signal. The filtered signal is displayed to provide a signal indicative of the patient's electrocardiographic activity. Certain numerical measurements, including $V_{rms40}$, LASD and QRS complex duration can also be computed and displayed. It has been found experimentally that adaptive filtering utilizing the present invention can be completed in as few as 20 ECG cycles.

In a preferred embodiment, the ECG signals are acquired with concentric electrodes and the signals are sampled and digitized at a rate of 1000 Hz. Also in a preferred embodiment, the signals are processed to reduce low frequency signal components utilizing a multiple pole zero phase shift filter algorithm. Further, in a preferred embodiment common mode signals are reduced using a 60 Hz Harmonic Reduction Algorithm, feedback coefficients are determined using a Feedback Approximation Algorithm, bias weights are initialized using a Bias Weight Initialization Algorithm and the signals are filtered using a Time-Sequenced Adaptive Filtering Algorithm, as these algorithms are defined in this patent application.

DETAILED DESCRIPTION OF THE PREFERRED EMBODIMENTS

Figure 1:
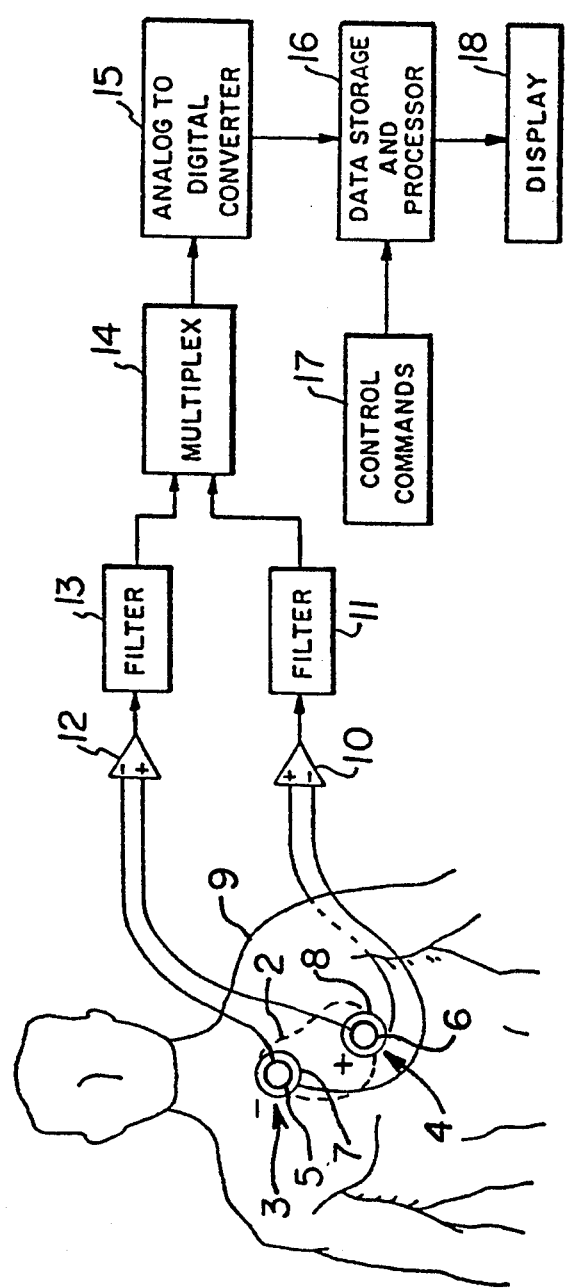
FIG. 1 is a block diagram showing the major components of the ventricular late potential detection apparatus of the present invention.

FIG. 1 is a block diagram of one embodiment of a ventricular late potential signal detection system in accordance with the present invention. This application requires at least two high gain, high frequency ECG signals; one is used as the input signal, the other as the reference signal as described below. The necessary ECG signals are obtained via electrodes placed on the surface of the thorax of the patient.

In a preferred embodiment, concentric electrodes are utilized, as described in my copending application entitled "Concentric Electrode For Use In Detecting Low Level Bioelectric Signals" which is incorporated herein by reference. The concentric electrodes allow for recording of two ECG signals with QRS activity of very similar morphology, or shape of the underlying ECG waveform. This is particularly important in the terminal portion of the QRS. With adequate separation between the inner electrode and outer ring, the noise is sufficiently uncorrelated. As shown in FIG. 1, a patient has two concentric electrodes positioned on the surface of the chest near the heart 2, shown in phantom, to acquire two ECG signals. A first concentric electrode 3 is placed at about the second right intercostal space. A second concentric electrode 4, identical to electrode 3, is placed at or about a point over the apex of the heart 2. For purposes of clarity, only two electrode pairs have been shown in FIG. 1, however, any number of electrode pairs greater than one can be used in this invention.

When two electrodes are used, as shown in FIG. 1, two differential signals are produced. One differential signal is the difference in potential between the two center electrodes 5, 6 obtained by connecting them to a differential amplifier 12. The second differential signal is the difference in potential between the outer ring electrodes 7, 8 obtained by connecting them to another differential amplifier 10. Both amplifiers 10, 12 have the same gain, usually on the order of 2000.

The differential analog signals or outputs from differential amplifiers 10, 12 are then bandpass filtered by filters 11 and 13, respectively, to remove the low frequency components of the ECG so that each output has a bandwidth of approximately 0.05 Hz to 400 Hz. This upper limit is higher than that of standard ECG preamplifiers to preserve the high frequency ventricular late potentials. The two bandpass filtered differential analog signals, along with any other ECG signals provided to facilitate diagnosis, are preferably sequenced by a multiplexer 14 for a standard analog-to-digital converter 15. Alternatively, each differential signal may be digitized by separate analog-to-digital converters, eliminating the multiplexer 14.

Each of the two bandpass filtered analog signals are sampled and digitized at a rate that exceeds the Nyquist rate, which is twice the highest frequency component in the signal and is the theoretical minimum rate that ensures recovery of the signal. Since filters 11 and 13 effectively eliminate frequency components over about 400 Hz, the maximum frequency component in the signals is approximately 400 Hz and the Nyquist rate for this system is, therefore, at least 800 Hz. Thus, a sampling rate per bandpass filtered analog signal of 1000 Hz has been selected as being adequate.

Both of the now digitized signals are transmitted to a computer 16 for storage and processing. Both signals, before processing or after, can be reviewed on a display 18. Processing is selected and initiated by control commands 17.

Figure 2:
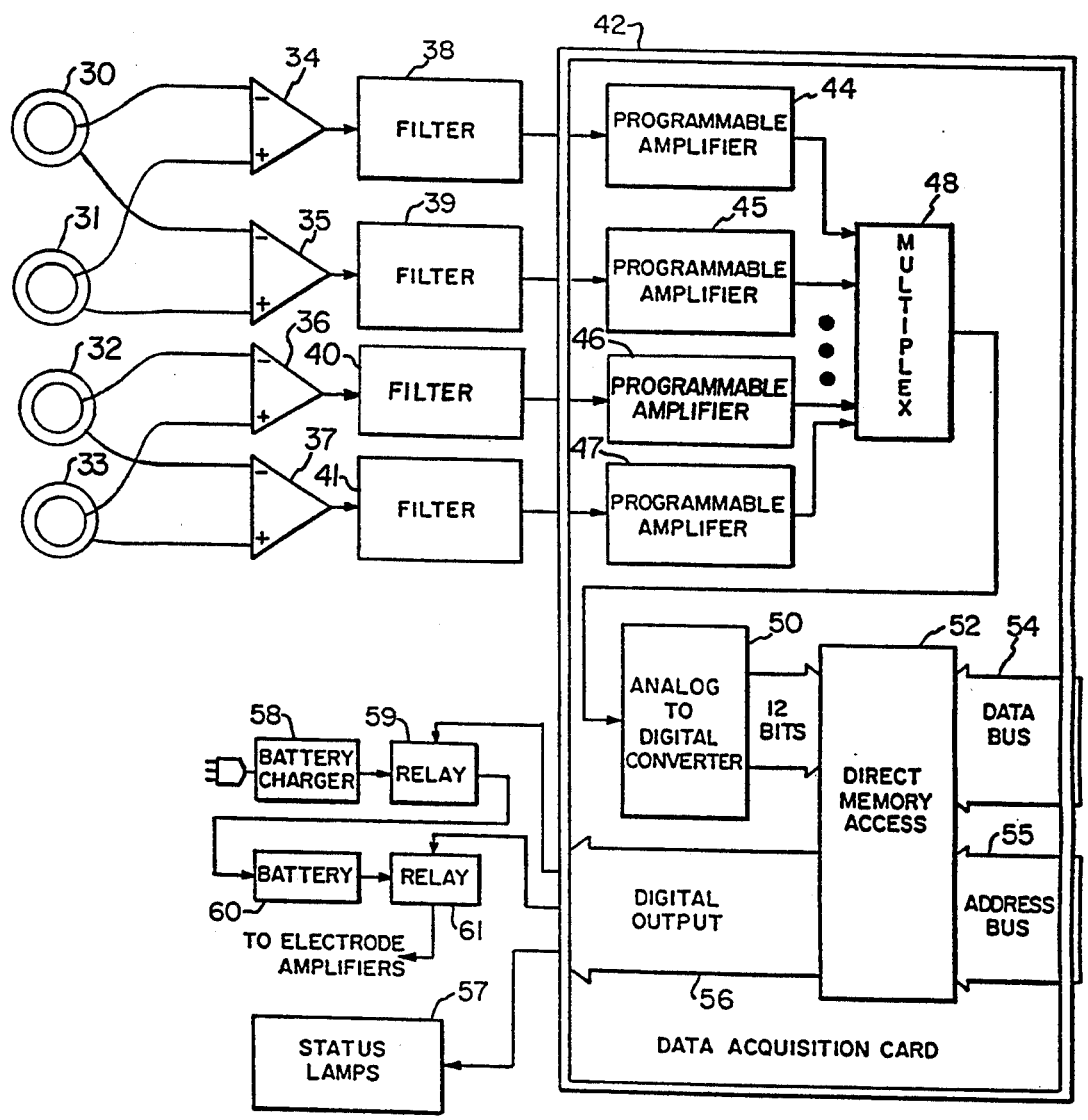
FIG. 2 is a block diagram of the data acquisition portion of the system shown in FIG. 1 showing a plurality of concentric electrode pairs.

FIG. 2 is a more detailed block diagram of the data acquisition portion of the system shown in FIG. 1. FIG. 2 shows a plurality of concentric electrodes, used in pairs. The first pair is shown as 30 and 31; the $n^{th}$ pair is shown as 32 and 33. The analog signals acquired by these surface electrodes are amplified (differential amplifiers 34, 35, 36 and 37) and filtered (bandpass analog filters 38, 39, 40 and 41). While the exact frequency range is not critical to the present invention, in a preferred embodiment each signal has frequency components in the frequency range from about 0.05 Hz to 400 Hz. The bandpass filtered analog signals are transmitted to a data acquisition card 42.

In a commonly available data acquisition card, each analog signal is supplied to a programmable amplifier. As shown in FIG. 2, the signal from bandpass filters 38, 39, 40 and 41 are supplied to programmable amplifiers 44, 45, 46 and 47, respectively. It is to be understood that there is a differential amplifier, bandpass filter, and programmable amplifier corresponding to each signal acquired by each pair of concentric electrodes.

The analog signals amplified by the programmable amplifiers are sequentially transmitted by the multiplexer 48 to an analog-to-digital converter 50. Each signal is sampled and digitized at a rate at least equal to the Nyquist rate. In one experimental system, data is represented by a 12 bit format. In the preferred embodiment, data would be represented by a 16 bit format, and might shift to a higher number based on the state of the art. The digitized signals are transferred to the central processor for storage in random access memory by a direct memory access 52.

The direct memory access 52 is a well known portion of the data acquisition card 42 and is used to store the incoming data, to supply information between the direct memory access 52 and the central processor via a data bus 54 and an address bus 55, or to pass an output signal along a digital output bus 56. Certain information can be displayed from the central processor through the direct memory access 52 and the digital output bus 56 to one or more status lamps 57. Additional information can be used to control a battery charger 58, a first safety relay 59, a battery 60, and a second safety relay 61. The output of the second safety relay 61 is supplied to the differential amplifiers 34, 35, 36 and 37. The use of safety relays 59 and 61 is a safety feature to ensure that the charger 58 is disconnected from the battery 60 when the system is in use and the system is inoperable when the batteries are being charged.

Figure 3:
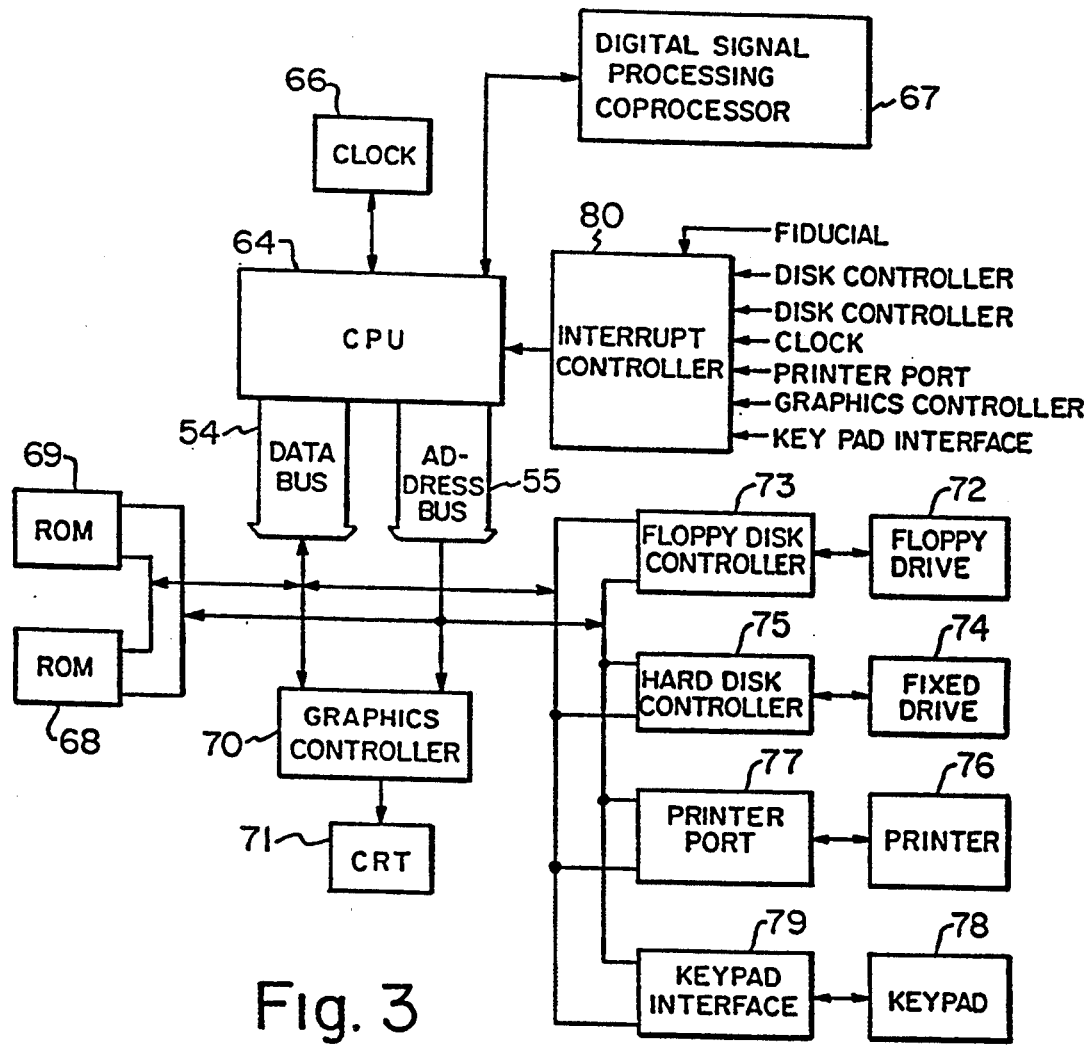
FIG. 3 is a block diagram of the remainder of the system shown in FIG. 1.

FIG. 3 shows a block diagram of the central processing portion of the system which is joined to the data acquisition portion of the system of FIG. 2 via the data bus 54 and the address bus 55. A central processing unit or CPU 64 receives and transmits data and addresses to the remainder of the system by way of the data bus 54 and the address bus 55. A clock 66 provides required timing information to the CPU 64. A digital signal processing coprocessor 67 may also be used in conjunction with the CPU 64 to help speed up the activities of the CPU 64. The system also includes a random access memory 68 and a read-only memory 69, both connected to the data bus 54 and the address bus 55. In addition, a graphics controller 70, connected to the data bus 54 and the address bus 55, controls the system output which is shown on a cathode ray tube (CRT) display 71 or the like. Data can be supplied to and taken from the CPU 64 or the memories by means of a floppy disk drive 72 and a floppy disk controller 73, a fixed drive 74, and associated hard disk controller 75, a printer 76 and associated printer port 77 and a keypad 78 and associated keypad interface 79. The floppy disk controller 73, hard disk controller 75, printer port 77, and keypad interface 79 are each connected to the data bus 54 and the address bus 55.

Rather than have the CPU 64 periodically poll all of the various elements to determine whether any condition requiring immediate action has developed, it is preferable to directly control the CPU 64 by means of an interrupt controller 80. Interrupt controls that are useful in the present invention are a floppy disk controller interrupt, a hard disk controller interrupt, a clock interrupt, a printer port interrupt, a graphics controller interrupt, and a keypad interface interrupt. The fiducial interrupt shown in FIG. 3 is a special command which will be explained in more detail in connection with FIG. 4.

In analyzing the measured surface ECG information in a preferred embodiment of the present invention, it is necessary to determine at least one easily identifiable reference or trigger point in each of the underlying ECG signals, such as the QRS complex, P-wave, etc. This triggering is controlled by preferably detecting the location of the QRS complex within the measured ECG signal. The QRS complex is very distinct and is of much greater magnitude than the ventricular late potential and is therefore easy to detect and use as a trigger point for further filtering or processing of the measured data. In a preferred embodiment of the invention, the detection of the QRS complex is carried out by the system software and no separate detection of these signals is necessary. In an alternative embodiment, it is possible to use a hardware trigger to detect the QRS complex and to create what is referred to as a fiducial interrupt signal which would be supplied to the interrupt controller 80 of FIG. 3.

Figure 4:
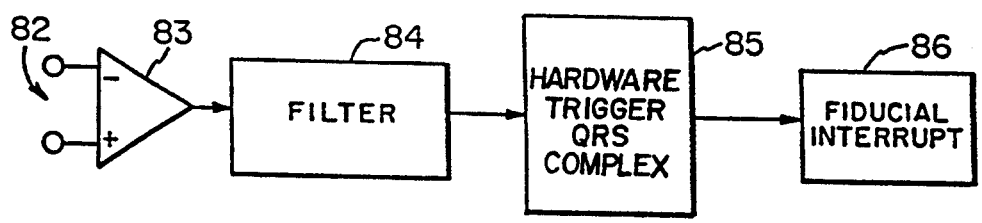
FIG. 4 is a block diagram of a hardware trigger.

FIG. 4 illustrates one arrangement utilizing a hardware trigger. This arrangement includes a surface electrode pair 82 whose output is supplied to an amplifier 83, a filter 84 and a hardware trigger 85. The hardware trigger 85 generates a trigger output signal when the QRS complex is detected and creates a fiducial interrupt signal 86 which is supplied to the interrupt controller 80 in FIG. 3.

Once the surface ECG analog signals have been acquired and digitized in accordance with the hardware and/or software discussed in FIGS. 1–4 above, remainder of the analysis of and computation on the acquired data will be conducted, preferably, in programmed multipurpose digital CPU 64 as shown in FIG. 3. Essentially the elements of a system would include a microprocessor with read only memory, a random access memory, a display, a control program and control switches. The control program can either be stored in hard disk and loaded into the random access memory 68 whenever the procedure is started or the program could be burned directly into the read only memory 69 and thereafter used by the CPU 64. Preferably, the ECG analog signals measured at the thorax of the patient are digitized and supplied directly to the random access memory 68 where it is thereafter used by the CPU 64.

Figure 5A:
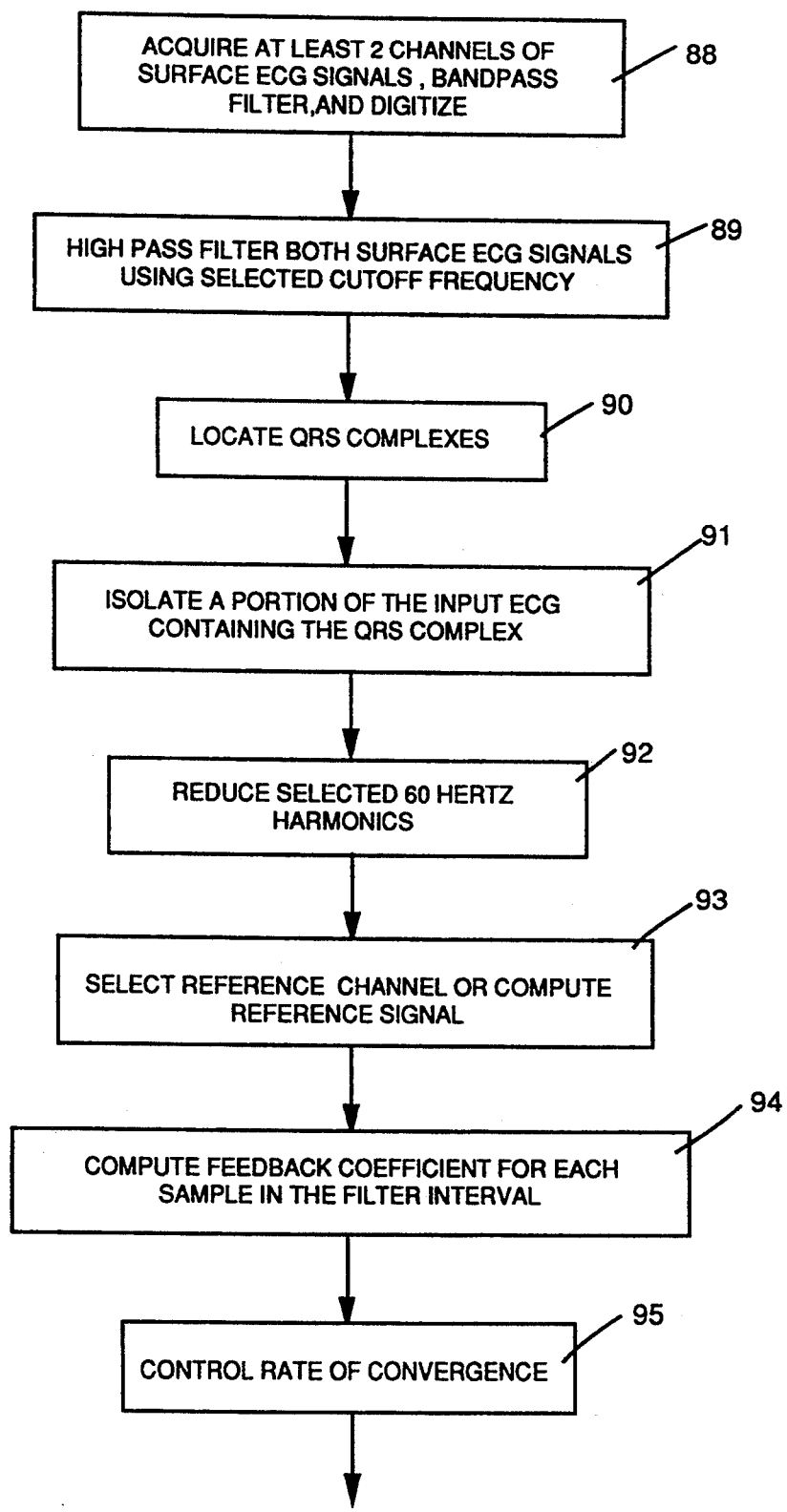
FIGS. 5A and 5B are a flow chart of the main control program in accordance with the present invention.
Figure 5B:
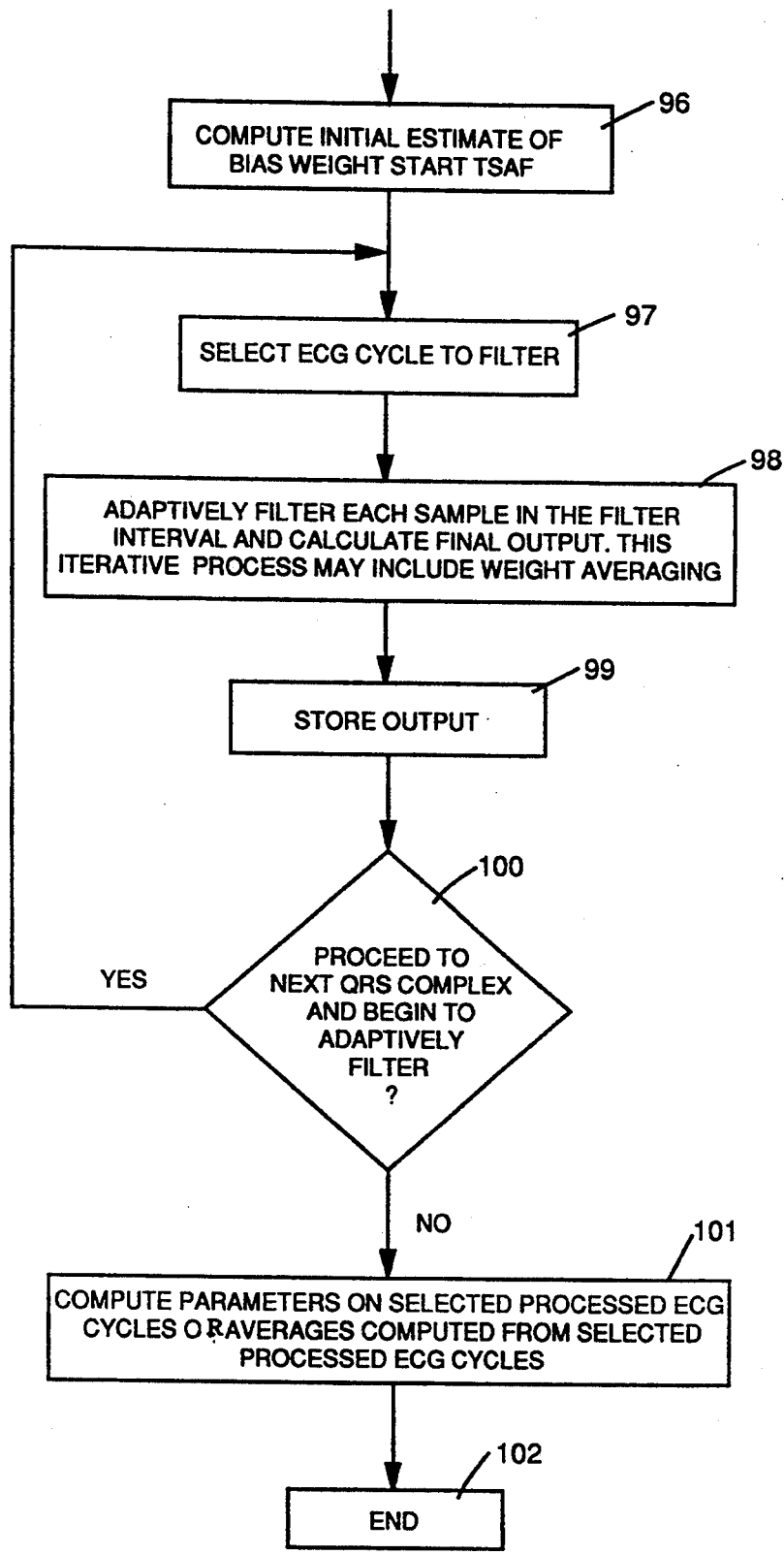

FIGS. 5A and 5B are a flow chart of the main control program in accordance with the present invention. As an overview of the flow chart of FIGS. 5A and 5B, the general scheme of the present invention is to: 1) reduce low frequency components in the ECG signals; 2) reduce common mode signals; 3) compute feedback coefficients; 4) initialize bias weights; and 5) time-sequence adaptively filter the ECG signal, optionally with weight averaging, whereupon the ventricular late potentials are identified and either displayed or computations confirming their presence (i.e., $V_{rms40}$; LASD and duration of QRS complex) are made.

The adaptive filtering carried out in the present invention is based on a known technique for filtering noise from a repetitive or cyclic signal when a second signal having a highly correlated base signal, but uncorrelated noise, is available. The second signal is used as a reference signal. A time period or "filter window" comprising all or part of the ECG waveform and containing the ventricular late potential is adaptively filtered utilizing the reference signal as a basis for filtering. The filter window is subdivided into filter intervals, and each filter interval has its own adaptive filter algorithm and includes one or more sample points. After the primary or input channel has been adaptively filtered for each selected filter interval, this filtered data or modified data is saved for later display or analysis or storage. The program then searches for the next ECG signal which in turn is filtered and the data is stored and/or manipulated.

More specifically, unlike a fixed frequency filter algorithm, an adaptive filter algorithm employs an algorithm which continuously adjusts and adapts the filter's parameters during operation according to some predetermined criteria, to optimize the filter's performance. The adjustable parameters of an adaptive filter algorithm are called "weights". The weights can be discreet values or can be part of a weight matrix. Weights are modified by an iterative procedure which requires only minimal a priori knowledge about the signal. The adaptive filter algorithm adjusts the weights according to the predetermined criteria so that the output after filtering is an optimized estimate of the signal. Each adaptive filter algorithm of each filter interval "learns" the characteristics of the input signal for that interval. It is desirable that this occur using as few cardiac cycles as possible. Feedback coefficients employed as part of the filtering algorithm control the rate of "learning" or adaptation which is also commonly referred to as "convergence". The higher the feedback coefficient, the faster the convergence. Additionally, bias weights can also be employed when adaptively filtering as a component of the adaptive filter algorithm. Bias weights are simply a mechanism to achieve more consistent signal representation.

In accordance with the present invention, first, as shown in step 88 of FIG. 5A, at least 2 channels of ECG analog signals are acquired from the surface of the patient's thorax. The analog signals are filtered with a bandpass filter. The preferred bandpass filter has a lower cut-off frequency of 0.5 Hz and an upper cut-off frequency of about 400 Hz so that each output after filtering has a bandwidth of approximately 0.5 Hz to 400 Hz.

The filtered analog signals are sampled and digitized utilizing the above-described hardware and/or software as shown in step 88. Sampling is conducted at a rate at least equal to the Nyquist rate as described above. This is to prevent aliasing. In a preferred embodiment, the sampling rate is 1000 Hz per signal, which in turn equals one sample point per millisecond.

Second, as shown in step 89, both of the now digitized ECG signals are processed to remove low frequency noise components of the ECG signals. These noise components can be reduced in several different ways. The present invention utilizes a digital high pass filter algorithm using selected cut-off frequencies to remove the low frequency components of the ECG signals. The preferred filter is a four pole, zero phase shift filter algorithm. The cut-off frequency for this filter is selectable, but is preferably 25 Hz, thus eliminating low frequencies below 25 Hz from the digitized ECG signals. QRS complexes are located within each ECG signal as shown in step 90, and are used to provide the easily identifiable reference point discussed above. Only a portion of the ECG signal, approximately a 400 millisecond filter window, about and containing the QRS complex, is adaptively filtered. Therefore, this portion must be identified and located as indicated in step 91.

Third, as shown in step 92, common mode interference, 60 Hz and/or harmonics, is reduced utilizing a single least-mean-squared-enhancer as described and hereinafter referred to as the 60 Hz Harmonic Reduction Algorithm.

If common mode interference is present, it should be reduced prior to applying the TSAF for optimal results. There are numerous methods for reducing these components. In the current embodiment, 60 Hz harmonics are removed with separate adaptive filters (algorithms), implemented by the following equations:

(a) equations generating two representations of a 60 Hz harmonic, the representations being 90 degrees out of phase:

$$sine = A*sin(2*pi*N*60*i/f_s) \text{ and} \qquad (1)$$

$$cosine = A*cos(2*pi*N*60*i/f_s + pi/2) \qquad (2)$$

where
pi=3.1416,
N=a whole number determining the 60 Hz harmonic, and
$f_s$=the sampling frequency of the ECG signals; (b) the algorithm to reduce the 60 Hz harmonic is implemented by the following equations on consecutive input signal samples; let ecg(i)=the acquired and digitized ECG signal possibly containing 60 HZ harmonics,
$ecg_f(i)$=ECG signal after filtering to reduce 60 Hz harmonic,
$w_{sine}$=adaptive filter weight,
$w_{cosine}$=adaptive filter weight, and
$u_{harmonic}$=the feedback coefficient controlling convergence rate of filter; then $$ecg_f(i) = ecg(i) - w_{sine}*sine - w_{cosine}*cosine; \qquad (3)$$

$$w_{sine\ next} = w_{sine} + 2*u_{harmonic}* ecg_f(i)*sine; \qquad (4)$$

$$w_{cosine\ next} = w_{cosine} + 2*u_{harmonic}* ecg_f(i)*cosine; \text{ and} \qquad (5)$$

increment i which moves the process to the next sample point; return to equation (1) or stop if at end of signal.

Care must be exercised in applying the 60 Hz Harmonic Reduction Algorithm to control the rate at which the weights of the adaptive algorithm adapt, in order to prevent distortion to the morphology of the QRS complex, particularly onset and offset, which can occur if the adaptive filter weights are allowed to adapt, without constraint, over the QRS complex. The control procedure starts in a "forward" direction, in a filter interval of the digitized ECG signal that precedes the QRS complex by at least 40–50 milliseconds. The algorithm's feedback coefficient $u_{harmonic}$ is initially set to a high value for rapid convergence. After a short time period of perhaps 20 samples or 20 milliseconds, the feedback coefficient $u_{harmonic}$ is heavily reduced for slow convergence. Filtering proceeds "forward" into the onset of the QRS complex and stops. Then a filter interval of the digitized ECG signal approximately 200 milliseconds after the QRS complex is located. The filtering process begins again and proceeds "backwards" in time on successive filter intervals toward the offset of the QRS complex and continues on and into the same QRS complex and stops, whereupon common mode interference is successfully filtered out of the digitized ECG signal. The foregoing analysis will be hereinafter referred to as the "60 Hz Harmonic Reduction Algorithm".

As shown in step 93, noise in each of the two digitized ECG signals is estimated, and a reference signal and an input signal are selected based upon the estimated noise levels as follows. Using the located QRS complexes as reference points in the ECG, a portion of the digitized ECG signals is selected where no ECG activity occurs. Both the location of this portion of the ECG cycle and the duration of the portion (usually between 50 and 200 milliseconds) are selectable Electrical noise is then estimated in each ECG signal using these portions. The signal with the lesser estimated noise, based on the standard deviation is selected as the reference channel as indicated at step 93. Alternatively, the reference ECG signal can be computed by summing sample points (shown in equation #9). The remaining ECG signal is the input signal.

Although at this point the process has eliminated both the low frequency components and the common mode interference, certain determinations must be made before TSAF can begin. Specifically: 1) a unique feedback coefficient $u_i$ for the TSAF algorithm, which controls the rate of change of the adaptive filter weights, must be computed for each filter interval of the digitized ECG signal wherein TSAF is to be applied; 2) the rate of convergence of the adaptive filter weights of the TSAF algorithm must be controlled, similar to the convergence control process for the filtering of common mode interference; and 3) an initial estimate of the bias weight of the TSAF algorithm must be made.

As indicated in step 94, the unique feedback coefficient $u_i$, which is associated with each filter interval, is computed for each filter interval in the filter window. Once computed, each unique feedback coefficient $u_i$ for each filter interval can be used to control the rate of convergence of the TSAF algorithm as shown in step 95 and to compute the initial estimate of the bias weight of the TSAF algorithm as shown in step 96. Thus assuming a sampling rate of 1000 samples per second, each of the 400 filter intervals or sample points in the selected 400 millisecond filter window of the digitized ECG input signal has its own unique feedback coefficient $u_i$ and in turn, its own unique TSAF algorithm.

The following equations define the processing of one filter interval within the filter window of a digitized ECG input signal to compute the primary input vector, the reference input vector and the weight vector for sample point i in the filter window.

$$ECG_1(i) = [ecg_1(i-n) \ldots ecg_1(i) \ldots ecg_1(i+n)]^T; \quad (7)$$

$$ECG_2(i) = ecg_2(i) \text{ for } m=0; \quad (8)$$

$$ECG_2(i) = [ecg_2(i-m) + \ldots + ecg_2(i) + \ldots + ecg_2(i+m)]/(2m+1) \text{ for } m>0; \text{ and} \quad (9)$$

$$W(i) = [w(i-n) \ldots w(i) \ldots w(i+n)]^T, \quad (10)$$

where:

$ecg_1(i)$ is the $i^{th}$ point in the filter window of the primary or input digitized ECG signal;

$ecg_2(i)$ is the $i^{th}$ point in the filter window of the reference digitized ECG signal;

m is the number of samples to the left or to the right of point of interest;

n is just a positive number so that $(2n+1)$ is the dimension of the primary input vector and the weight matrix; and T is a symbol indicating matrix transpose.

$ECG_1(i)$ is the primary input vector;

$ECG_2(i)$ is the reference input vector; and $W(i)$ is the weight vector, all for sample point i.

$ECG_2(i)$ could be equal just to $ecg_2(i)$. However, creating $ECG_2(i)$ reduces noise in the reference which improves overall noise reduction.

The filtered output is:

$$ecg_f(i) = ECG_1(i)^T * W(i), \text{ and the error is:} \quad (11)$$

$$error(i) = ECG_2(i) - ecg_f(i). \quad (12)$$

The weights are then updated for use in the next cycle by:

$$W(i)_{next \, cycle} = W(i) + 2 * u_i * error(i) * ECG_1(i), \quad (13)$$

where $u_i$ is a feedback coefficient that controls the size of change of $W(i)$.

The parameter matrix $W(i)$ is not used again until filtering the $i^{th}$ point in the next ECG cycle, and $u_i$ is separately defined for every filter interval in the filter window.

For the present invention, it is important that individual adaptive filter algorithms at each filter interval in the filter window converge at the same rate and this must be controlled as shown at step 95 using the feedback coefficient approximation algorithm, defined as follows. To ensure stability and equivalent convergence rates, an estimate of the feedback coefficient can be computed as:

$$u_i = \beta * [ecg_1(i)_{ave}^2 + \sigma_{noise}^2]^{-1} * (2*n+1)^{-1}, \quad (14)$$

where:

$ecg_1(i)_{ave}^2$ is the squared value of the average of $ecg_1(i)$ computed from several beats n, (the beats and number are selectable);

$\sigma_{noise}$ is the standard deviation of the noise in the acquired signal estimated over a diastolic segment of the ECG; and $\beta$ is a positive fraction. In this application, an appropriate value for $\beta$ is 0.015.

The above-described process of computing an approximate value for the feedback coefficient $u_i$ using the squared value of the average and an estimate of the noise is referred to as the Feedback Coefficient Approximation Algorithm.

Convergence on as few cycles as possible is desired, but as previously indicated, stability requirements limit the magnitude of each $u_i$. To increase the number of iterations for a given number of cycles, $W(i)$ is not updated just in the prior ECG cycle, but also within the current cycle where it is used for filtering. $W(i)$ is computed on the previous cycle. In the current cycle, $ECG_2(i)$ is computed and varied according to the following two equations depending on the update or iteration. Where m is the number of filter intervals to the left or right of the filter interval of interest. for $m=0$, let $$ECG_2(i-1) = ecg_2(i-1); \text{ and} \quad (15)$$

$$ECG_2(i+1) = ecg_2(i+1); \quad (16)$$

for $m>0$;

$$ECG_2(i-1) = [ecg_2(i-m-1) + \ldots + ecg_2(i-1) + \ldots + ecg_2(i+m-1)]/(2m+1); \text{ and} \quad (17)$$

$$ECG_2(i+1) = [ecg_2(i-m+1) + \ldots + ecg_2(i-1) + \ldots + ecg_2(i+m+1)]/(2m+1). \quad (18)$$

The first iteration in the current cycle is:

$$error(i)' = ECG_2(i-1) - ECG_1(i)^T * W(i); \quad (19)$$

and $$W(i)' = W(i)' = W(i) + 2 * u_i * error(i) * ECG_1(i). \quad (20)$$

The second iteration in the current cycle is:

$$error(i)'' = ECG_2(i+1) - ECG_1(i)^T * W(i)'; \quad (21)$$

and $$W(i)'' = W(i)' + 2 * u_i * error''(i) * ECG_1(i). \quad (22)$$

The filtered value of the $i^{th}$ filter interval is now computed and is:

$$ecg_f(i) = ECG_1(i)^T * W(i)''; \text{ also} \quad (23)$$

$$error(i) = ECG_2(i) - ECG_1(i)^T * W(i)''; \text{ and} \quad (24)$$

$$W(i)_{next \, cycle} = W(i)'' + 2 * u_i * error(i) * ECG_1(i). \quad (25)$$

This, in effect, reduces the needed cycles by approximately a factor of three.

Lastly, highpass filtering during acquisition and digital frequency filtering prior to adaptive filtering places the baseline at or very near zero amplitude. All weights associated with isopotential segments should be equal and approach zero. In some instances, filtered data indicated that weights were at some value above zero possibly due to some correlation in the noise between signals or some offset in the baseline levels of the ECG signals. To drive the weights to zero, an average value for each weight across an isopotential segment is computed and is subtracted from all weights in the filter interval.

$$W_{ave} = [W(i) + W(i+1) + \ldots + W(i+k)] * k^{-1} \quad (26)$$

$$W(i) = W(i) - W_{ave} \times C \quad (27)$$

where k is the number of weights that are selected for computing the average weight and C is some value from 0 to 1, preferably 0.05. This improves the baseline and minimally affects electrocardiographic activity in the filter interval; however, low amplitude signal components may be affected. As indicated above, the feedback coefficients control rate of adaptation, i.e., the higher the feedback coefficient, the faster that adaptation. While rapid convergence is desirable, there is an upper limit on the magnitude of the feedback coefficient; if the magnitude exceeds this limit, the system becomes unstable. Since convergence occurs in a geometric manner, the present invention increases the number of iterations for a given number of cycles. In contrast to Ferrera's method which would update each weight matrix and bias weight in the previous cardiac cycle for use in filtering the next cycle, each weight matrix and bias weight are now updated not only in the previous ECG cycle but also within the current cycle.

Inclusion of a bias weight in the TSAF algorithm can significantly enhance the results, however it can also significantly increase acquisition time since more data is needed to get the filter to converge. If better signal quality is desired without significantly extending acquisition time, a procedure as indicated by step 96 can be used to provide an initial value for the bias weight $w_b(i)$ for each point i in the filter interval. Two such procedures are:

1) Using the adaptive filtering procedure outlined above, compute output values for several ECG cycles, the number of cycles to exceed the number necessary for the filter to converge to some satisfactory level of performance. Using the cycles processed after the filter has converged, compute the average of the outputs. Assign $w_b(i)$ the value of the average of the outputs for point i, i.e., $$w_b(i) = [ecg(i)_{beat\ j} + \ldots + ecg(i)_{beat\ k}]/(k-j+1) \quad (28)$$

where beat j is the first beat where the filter is sufficiently converged and beat k is the last beat chosen for inclusion in the average.

2) Using the adaptive filtering procedure outlined above, compute output values for several ECG cycles, the number of cycles to exceed the number necessary for the filter to converge to some satisfactory level of performance. Use the cycles processed after the filter has converged. Assign $w_b(i)$ the following value according to the following condition, $$w_b(i) = ecg(i)_{beat\ j} \text{ such that} \quad (29)$$

Magnitude$[ecg(i)_{beat\ j}] <$ Magnitude$[ecg(i)$ beat k$]$ for any cycle k considered after the above filter has satisfactorily converged.

The second procedure above is used in the current implementation to provide an initial estimate of the bias weight. The filtering procedure described above in conjunction with the second procedure will be referred to as the Bias Weight Initialization Algorithm.

To institute TSAF utilizing the adaptive filter weights and the bias weights as described above, all other weights are reset to zero. The first iteration in the next cycle to filter is:

$$error(i)' = ECG_2(i-1) - ECG_1(i)^T * W(i) - w_b(i); \quad (30)$$

$$W(i)' = W(i) + 2*u_i*error(i)' * ECG_1(i); \text{ and}$$

$$Bias\ Weight = w_b(i)' = w_b(i) + 2*u_b* error(i)' \quad (32)$$

where $u_b$ is the feedback coefficient for modifying the bias weight.

The second iteration in the current cycle is:

$$error(i)'' = ECG_2(i+1) - ECG_1(i)^T * W(i)' - w_b(i)'; \quad (33)$$

$$W(i)'' = W(i)' + 2*u_i*error(i)''* ECG_1(i); \text{ and} \quad (34)$$

$$w_b(i)'' = w_b(i)' + 2*u_b*error(i)''. \quad (35)$$

The filtered output value of the $i^{th}$ point is now computed and is the product of the matrix transpose of the signal at point i times the adaptive filter weight matrix at point i plus the bias weight value at point i as follows:

$$ecg(i) = ECG_1(i)^T * W(i)'' + W_b(i)''; \text{ also} \quad (36)$$

$$error(i) = ECG_2(i) - ecg(i); \quad (37)$$

$$W(i)_{next\ cycle} = W(i)'' + 2*u_i*error(i) *ECG_1(i); \text{ and} \quad (38)$$

$$w_b(i)_{next\ cycle} = w_b(i)'' + 2*u_b* error(i)'. \quad (39)$$

Note that the feedback coefficient $u_b$ for modifying the bias weights is the same for each bias weight and is equal to $\beta$ which is defined previously. The above procedure using the initialized bias weight, multiple updates of the weight matrix and bias weight, and weight averaging is referred to as the Time-Sequenced Adaptive Filtering Algorithm.

Referring again to FIG. 5B, an ECG cycle to be filtered is selected as set out in step 97. As shown in step 98, each filter interval in the filter window is adaptively filtered. This output is stored, step 99. Either the next QRS complex in the next ECG cycle is filtered in a likewise manner, step 100, or parameters are computed in selected processed ECG cycles or on averages computed from selected processed ECG cycles, step 101, whereupon the results are displayed or stored and the process ends, step 102.

In a preferred embodiment of the present invention, only a portion of each cardiac cycle is adaptively filtered. This portion or filter window is about 400 milliseconds in length and contains the QRS complex. The duration of this filter window can be shorter or longer than 400 milliseconds, but must minimally include onset and offset of the QRS complex.

In a preferred embodiment, two ECG signals are acquired on the body surface by a pair of concentric electrodes in a frequency range of 0.05 Hz to 400 Hz. The ECG signals are sampled and digitized. The sampling rate is 1000 Hz per signal. Low frequency components and common mode interference are reduced. The signal with the lesser estimated noise is selected as the "reference" signal.

A filter window of approximately 400 milliseconds duration containing the QRS complex is selected in the remaining or "input" signal. The 400 millisecond filter window is adaptively filtered. The filter window is divided into filter intervals comprising one or more sample points. Either individual sample points or groups of sample points can have a unique adaptive filter, however, in the preferred embodiment, each filter interval equals one sample point, and each sample point is individually adaptively filtered. Each filter interval has a unique feedback coefficient. The weight matrix for each filter interval comprising a single sample point is a one by five matrix, i.e., it is composed of five weights. The feedback coefficient for a given filter interval is computed at the start of the filtering process. The feedback coefficient $u_i$ is calculated for each point i as the inverse of the sum of the magnitude squared of an average of the underlying signal at point i and an estimate of the variance of the noise in the input signal. To guard against instability in the weights particularly in areas of large signal change cycle-to-cycle weights are limited to a magnitude less than a selectable threshold; in this instance, no weight should exceed 0.5. To guard against "stalling" of the weights at a non-optimal value due to correlation of noise between the input signal and the reference signal, a percentage of the average of the weights in the interval where the noise estimate was computed earlier is subtracted from all the weights. The percent is selectable and has been experimentally set at five percent.

As indicated in step 101, after processing selected beats in the data, the apparatus provides the user with the option of averaging the beats. Numbers of beats and which beats are selected by the user. This apparatus makes the same measurements: 1) $V_{rms40}$, root-mean-squared (RMS) amplitude of the last 40 milliseconds of the QRS complex; 2) QRS duration; and 3) low-amplitude-signal-duration, LASD, either on a single cycle or on an average complex to confirm identification of the ventricular late potential.

The feedback coefficients are calculated after any digital preprocessing and prior to the adaptive filtering. Thereafter, the feedback coefficients are used without modification for a particular input signal.

While the weights in each weight matrix and also the bias weights are computed in an iterative manner, the weights must be initialized to some value at the start. To simplify matters, the initial weights in each weight matrix are all preferably set to zero. A separate procedure is used to compute an initial value for the bias weights. The weights quickly reach some number other than zero where appropriate so that the filter accurately represents the underlying signal.

The equations have been given for a physical situation using a pair of concentric electrodes. One could acquire signals simultaneously with multiple pairs of concentric electrodes placed in different positions on the surface of the body, process the signals from each pair of concentric electrodes, and analyze each processed output signal for late potentials.

One could use three pairs of concentric electrodes specifically positioned in an orthogonal X, Y and Z arrangement and process the signals from each separately. The processed signals about and containing the QRS complex from each can then be vectorially summed to form a resultant representing the cardiac vector. The same measurements can be done on resultant complexes computed from individual complexes in each lead or on a resultant computed from an average of the processed X, Y and Z signals.

If 60 Hz harmonics are present in both channels, these present a high level of correlated noise, a condition that can reduce the performance of the adaptive filter. If present in only one channel, this channel will probably be selected as the primary input channel. The presence of the 60 Hz harmonics in the primary channel will affect the feedback coefficients, causing them to be smaller than would be necessary; the consequence is slower convergence. Many times, 60 Hz harmonics are absent in the acquired signals. If absent, it is not necessary to use the 60 Hz Harmonic Reduction Algorithm. However, use of this algorithm on signals that do not contain 60 Hz harmonics will not degrade the signal.

The Weight Average Algorithm is effective in further reducing residual noise, particularly that caused by random noise correlated between channels. It can also reduce the effects of 60 Hz harmonics. However, this is not as desirable as first removing these components. Again, while the weight average algorithm improves output, it is not necessary that it be used.

It should be emphasized that the preferred embodiment employs a specific sequence of steps, i.e., location of QRS complexes, reduction of low frequency components, reduction of selected 60 Hz harmonics, computation of feedback coefficients, initialization of bias weights and, lastly, time-sequenced adaptive filtering which may include weight averaging.

Figure 6A:
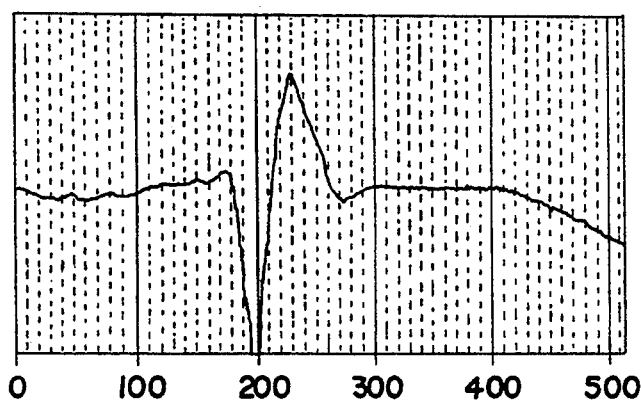
FIGS. 6A, 6B and 6C are a series of three graphs showing: 1) the input ECG as acquired with a completely obscured ventricular late potential (6A); 2) the input ECG signal after low frequency and common mode filtering (6B); and 3) the input signal after TSAF, clearly showing the presence of a ventricular late potential (6C).
Figure 6B:
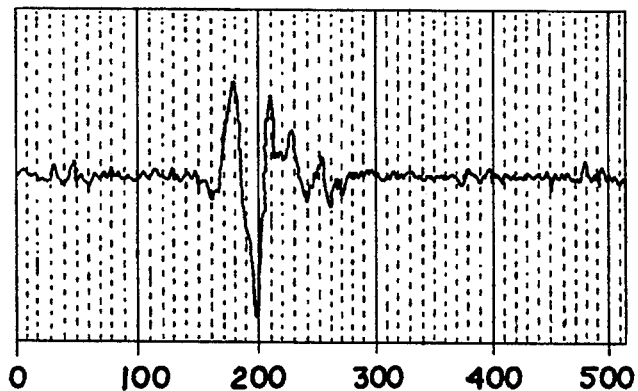
Figure 6C:
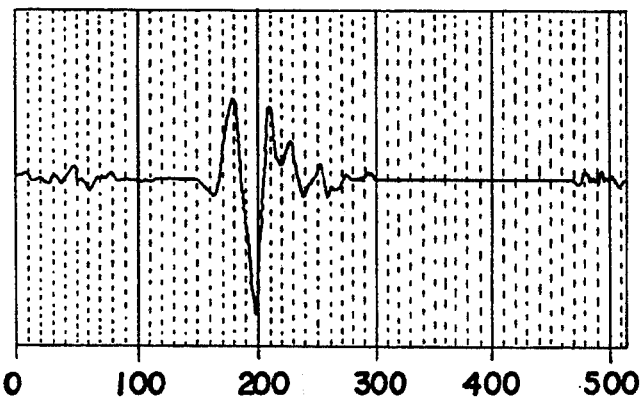

An apparatus in accordance with the present invention using a five weight matrix and one pair of concentric electrodes was built and tested. The results of one test are set forth in FIG. 6 where three average complexes are shown by FIGS. 6A, 6B and 6C. FIG. 6A discloses the primary input as acquired. FIG. 6B shows the primary input after high-pass filtering and reduction of 60 Hz harmonics. FIG. 6C shows the output after TSAF. It is clearly evident in FIG. 6C that QRS ends at 300 milliseconds. $V_{rms40}$ for FIG. 6C is 5.5 microvolts, QRS duration is 151 milliseconds and LASD for FIG. 6C is 75 milliseconds, indicating the presence of a ventricular late potential which clearly could not be identified from either of FIGS. 6A or 6B.

Having described above the presently preferred embodiments of the present invention, it is to be understood that it may be otherwise embodied within the scope of the appended claims.

I claim:

1. A method of detecting late potentials at the surface of a patient comprising the step of:
    (a) acquiring two or more ECG signals at a plurality of external locations on the surface of a patient;
    (b) filtering the surface ECG signals with a bandpass filter;
    (c) digitizing the acquired ECG signals by continuous sampling at a rate equal to or greater than the Nyquist rate;
    (d) storing the digitized ECG signals;
    (e) processing the digitized ECG signals to reduce low frequency signal components;
    (f) selecting a reference signal with the remaining ECG signals referred to as input signals and selecting a filter window in an ECG cycle from one or more of the digitized ECG input signals and defining filter intervals within said filter window;

(g) calculating a feedback coefficient $u_i$ associated with an adaptive filter algorithm for each filter interval within a filter window in an ECG cycle from one or more of the digitized ECG input signals;

(h) initializing a bias weight associated with an adaptive filtering algorithm for each filter interval by computing an initial value for the bias weight associated with the filter interval;

(i) thereafter adaptively filtering in time-sequenced manner selected filter intervals of the input signals; and (j) displaying or storing the results of the adaptive filtering step.

2. The method of claim 1 wherein the ECG signals are acquired using two or more concentric electrodes.

3. The method of claim 1 wherein the bandpass filter has a lower cut-off frequency of 0.5 Hz and an upper cut-off frequency of about 400 Hz so that each output after filtering has a bandwidth of approximately 0.5 Hz to 400 Hz.

4. The method of claim 1 wherein the ECG signals are digitized at a rate of 1000 Hz.

5. The method of claim 1 wherein the processing of the digitized ECG signals to reduce low frequency signal components utilizes a multiple pole, high-pass zero-phase shift filter algorithm.

6. The method of claim 5 wherein the cut-off frequency of the multiple pole, high-pass zero phase shift filter algorithm is selectable.

7. The method of claim 1 wherein the digitized ECG signals are processed to reduce common mode signals.

8. The method of claim 7 wherein the step of processing the digitized ECG signals to reduce common mode signals utilizes a 60 Hz Harmonic Reduction Algorithm where:

$$\text{sine} = A*\sin(2*pi*N*60*i/f_s + pi/2), \text{ and} \quad (1)$$

$$\text{cosine} = A*\cos(2*pi*N*60*i/f_s + pi/2), \quad (2)$$

are two representations of a 60 Hz harmonic, the representations being 90 degrees out of phase; the algorithm to reduce the 60 Hz harmonic is implemented by the following equations on consecutive input signal samples:

$$ecg_f(i) = ecg(i) - w_{sine}*\text{sine} - w_{cosine}*\text{cosine}; \quad (3)$$

$$w_{sine} \text{ next} = w_{sine} + 2*u_{harmonic}*ecg_f(i)*\text{sine}; \quad (4)$$

$$w_{cosine} \text{ next} = w_{cosine} + 2*u_{harmonic}*ecg_f(i)*\text{cosine; and} \quad (5)$$

increment i which moves the process to the next sample point; return to equation (1) or stop if at end of signal; (6)

where pi is 3.1416, N is a whole number determining the 60 Hz harmonic, $f_s$ is a sampling frequency of the ECG signals, ecg(i) is an acquired and digitized ECG signal, $ecg_f(i)$ is an ECG signal after filtering to reduce 60 Hz harmonic, $w_{sine}$ is an adaptive filter weight, $w_{cosine}$ is an adaptive filter weight, $u_{harmonic}$ is a feedback coefficient controlling convergence rate of the filter.

9. The method of claim 1 wherein the step of calculating the feedback coefficient $u_i$ for any filter interval in the filter window utilizes a Feedback Approximation Algorithm as defined by:

$$u_i \beta * [ecg_1(i)_{ave}^2 + \sigma_{noise}^2]^{-1} * (2*n+1)^{-1},$$

where $ecg_1(i)_{ave}^2$ is a squared value of the average $ecg_1(i)$ computed from several beats n, $\sigma_{noise}$ is a standard deviation of noise in the acquired signal estimated over a diastolic segment of the ECG, and $\beta$ is a positive fraction.

10. The method of claim 1 wherein the means for initializing the bias weight includes a Bias Weight Initialization Algorithm as defined by:

$w_b(i) = ecg_f(i)_{beat\ j}$, such that Magnitude $[ecg_f(i)_{beat\ j}]$ < Magnitude $[ecg_f(i)_{beat\ k}]$, for any cycle k considered after the filter has satisfactorily converged, where $w_b(i)$ is an initial value for the bias weight for each point i in the filter interval, $ecg_f(i)$ is an ECG signal after filtering, beat j is a first beat in the filter interval, beat k is a last beat selected for inclusion in the average, and where $w_b(i)$ is calculated after adaptive filtering has been applied to several ECG signals, the number of said several ECG signals being identified as the number necessary for said filter to converge to a desired level of satisfactory performance.

11. The method of claim 1 wherein the step of adaptively filtering in a time-sequenced manner filter intervals within a filter window utilizes a Time-Sequenced Adaptive Filtering Algorithm where:

1) a first iteration in a next cycle to filter calculates error(i)', W(i)' and Bias Weight as;

$$\text{error}(i)' = ECG_2(i-1) - ECG_1(i)^T * W(i) - w_b(i);$$

$$W(i)' = W(i) + 2*u_i*\text{error}(i)'*ECG_1(i); \text{ and}$$

$$\text{Bias Weight} = w_b(i)' = w_b(i) + 2*u_b*\text{error}(i)';$$

where error (i)' is a computed error of the first iteration, $ECG_2(i-1)$ is a reference input at $i-1$, $ECG_1(i)^T$ is a primary input matrix tranpose, $w_b(i)$ is the bias weight, W(i)' is a computed weight matrix of the first iteration, W(i) is a starting weight computed in the previous cycle, $u_i$ is a feedback coefficient, $ECG_1(i)$ is a primary input matrix, $w_b(i)'$ is a bias weight for the first iteration, and $u_b$ is a feedback coefficient for modifying the bias weight, 2) a second iteration in said cycle calculates error(i)″, W(i)″ and $w_b(i)$″ as;

$$\text{error}(i)'' = ECG_2(i+1) - ECG_1(i)^T * W(i)' - w_b(i)';$$

$$W(i)'' = W(i)' + 2*u_i \text{error}(i)''*ECG_1(i); \text{ and}$$

$$w_b(i)'' = w_b(i)' + 2*u_b*\text{error}(i)'';$$

where error*(i)″ is a compound error of the second iteration, $ECG_2(i+1)$ is a reference input at $i+1$, W(i)″ is a computed weight matrix at the second iteration, and $w_b(i)$″ is a bias weight for the second iteration, 3) a filtered output value of an $i^{th}$ point is determined as the produce of a matrix transpose of the signal at a point i times the adaptive filter weight matrix at point i plus the bias weight value at point i as follows;

$$ecg_f(i) = ECG_1(i)^T * W(i)'' + W_b(i)'',$$

error($i$) = $ECG_2(i) - ecg_f(i)$, $W(i)_{next\ cycle} = W(i)' + 2*u_i*$error($i$)$* ECG_1(i)$; and $w_b(i)_{next\ cycle} = w_b(i)'' + 2*u_b*$error($i$)', where $ecg_f(i)$ is a filtered output, error($i$) is the error at input i, $W(i)_{next\ cycle}$ is a weight matrix to use in a first iteration of the next cycle, $w_b(i)_{next\ cycle}$ is a bias weight to use in the first iteration of the next cycle.

12. The method of claim 11 wherein the adaptively filtered filter window includes all or a portion of one or more ECG cycles.

13. The method of claim 12 wherein the adaptively filtered filter window includes a portion of one or more ECG cycles, the portion being about and containing the QRS complex.

14. The method of claim 13 wherein the adaptively filtered filter window is about 400 milliseconds in duration.

15. The method of claim 1 wherein the adaptive filtering within each filter interval includes the steps of:
   (a) selecting a last computed value for the bias weight for the filter interval;
   (b) conducting a first updating of both a weight matrix associated with the adaptive filter algorithm and the bias weight for the input signal within the filter interval, using the reference signal for the preceding filter interval;
   (c) conducting a second updating of the weight matrix and the bias weight for the input signal of the filter interval using the reference signal of the subsequent filter interval;
   (d) calculating an output signal by multiplying the second updated weight matrix of the filter interval by the associated input signal, and adding the bias weight;
   (e) conducting a third updating of the weight matrix and bias weight of step (d) associated with the filter interval using the output calculated in step (d), and storing the third updating of the weight matrix and bias weight for use in a subsequent cycle.

16. The method of claim 15 wherein the filter interval is one sample point in duration and the weight matrix is a five element weight matrix.

17. The method of claim 1 wherein the display includes computation of predefined measurements of the patient's electrocardiographic activity either in fully processed individual beats or in averages of selected fully processed beats, wherein the number of beats is selectable.

18. The method of claim 17 wherein the display includes computation of the root mean squared amplitude of the last 40 milliseconds of a QRS complex within the filter interval.

19. The method of claim 17 wherein the display includes computation of the duration of QRS complex within the filter interval.

20. The method of claim 17 wherein the display includes computation of a low amplitude signal duration.

21. An apparatus for detecting late potentials at the surface of a patient comprising:
   (a) a means for acquiring two or more ECG signals at a plurality of external locations on the surface of a patient;
   (b) means for digitizing the acquired ECG signals by continuous sampling at a rate equal to or grater than the Nyquist rate;
   (d) a means for storing the digitized ECG signals;
   (e) a means for processing the digitized ECG signals to reduce low frequency signal components;
   (f) means for selecting a reference signal with the remaining ECG signals referred to as input signals and a means for selecting a filter window in an ECG cycle from one or more of the digitized ECG input signals and defining filter intervals within said filter window;
   (g) a means for calculating a feedback coefficient $u_i$ associated with an adaptive filter algorithm for each filter interval within a filter window in an ECG cycle from one or more of the digitized ECG input signals;
   (h) a means for initializing a bias weight associated with an adaptive filtering algorithm for each filter interval by computing a initial value for the bias weight associated with the filter interval;
   (i) a means for thereafter adaptively filtering in time-sequenced manner selected filter intervals of the input signals; and
   (j) a means for displaying or storing the results of the adaptive filtering step.

22. The apparatus of claim 21 wherein the ECG signals are acquired using two or more concentric electrodes.

23. The apparatus of claim 21 wherein the bandpass filter has a lower cut-off frequency of 0.5 Hz and an upper cut-off frequency of about 400 Hz so that each output after filtering has a bandwidth of approximately 0.5 Hz to 400 Hz.

24. The apparatus of claim 21 which further comprises a means for digitizing the ECG signals at a rate of 1000 Hz.

25. The apparatus of claim 24 wherein the means for processing the digitized ECG signals to reduce low frequency signal components utilizes a multiple pole, high-pass zero-phase shift filter algorithm.

26. The apparatus of claim 25 which further comprises a means to select the cut-off frequency of the multiple pole, high-pass zero phase shift filter algorithm.

27. The apparatus of claim 21 which further comprises a means to reduce common mode signals in the digitized ECG signals.

28. The apparatus of claim 27 which further comprises a means for processing the digitized ECG signals to reduce common mode signals, wherein said means utilizes a 60 Hz Harmonic Reduction Algorithm where:

$$\text{sine} = A*\sin(2*pi*N*60*i/f_s) \text{ and} \quad (1)$$

$$\text{cosine} = A*\cos(2*pi*N*60*i/f_s + pi/2), \quad (2)$$

are two representations of a 60 Hz harmonic, the representations being 90 degrees out of phase; the algorithm to reduce the 60 Hz harmonic is implemented by the following equations on consecutive input signal samples:

$$ecg_f(i) = ecg(i) - w_{sine}*\text{sine} - w_{cosine}*\text{cosine}; \quad (3)$$

$$w_{sine\ next} = w_{sine} + 2*u_{harmonic}*ecg_f(i)*\text{sine}; \quad (4)$$

$$w_{cosine\ next} = w_{cosine\ next} = w_{cosine} + 2*u_{harmonic}*ecg_f(i)*\text{cosine}; \text{ and} \quad (5)$$

increment i which moves the process to the next sample point; return to equation (1) or stop if at end of signal;

where pi is 3.1416, N is a whole number determining the 60 Hz harmonic, $f_s$ is a sampling frequency of the ECG signals, ecg(i) is an acquired and digitized ECG signal, $ecg_f(i)$ is an ECG signal after filtering to reduce 60 Hz harmonic, $w_{sine}$ is an adaptive filter weight, $w_{cosine}$ is an adaptive filter weight, $u_{harmonic}$ is a feedback coefficient controlling convergence rate of the filter.

29. The apparatus of claim 21 which further comprises a means for calculating the feedback coefficient $u_i$ for any filter interval in the filter window wherein said means utilizes a Feedback Approximation Algorithm as defined by:

$$u_i = \beta * [ecg_1(i)_{ave}^2 + \sigma_{noise}^2]^{-1} * (2*n+1)^{-1},$$

where $ecg_1(i)_{ave}^2$ is a squared value of the average $ecg_1(i)$ computed from several beats n, $\sigma$ noise is a standard deviation of noise in the acquired signal estimated over a diastolic segment of the ECG, and $\beta$ is a positive fraction.

30. The apparatus of claim 21 wherein the means for initializing the bias weight utilizes a Bias Weight Initialization Algorithm as defined by:

$$w_b(i) = ecg_f(i)_{beat\ j},$$

such that Magnitude $[ecg_f(i)_{beat\ j}] <$ Magnitude $[ecg_f(i)_{beat\ k}]$, for any cycle k considered after the filter has satisfactorily converged,
 where $w_b(i)$ is an initial value for the bias weight for each point i in the filter interval, $ecg_f(i)$ is an ECG signal after filtering, beat j is a first beat in the filter interval, beat k is a last beat selected for inclusion in the average, and
 where $w_b I$ is calculated after adaptive filtering has been applied to several ECG signals, the number of said several ECG signals being identified as the number necessary for said filter to converge to a desired level of satisfactory performance.

31. The apparatus of claim 21 which further comprises a means for adaptively filtering in a time-sequenced manner filter intervals within a filter window, where said means utilizes a Time-Sequenced Adaptive Filtering Algorithm where:
 a first iteration in a next cycle to filter calculates error(i)', W(i)' and Bias Weight as;

$$error(i)' = ECG_2(i-1) - ECG_1(i)^T * w_b(i);$$

$$W(i)' = W(i) + 2*u_i* error(i); \text{ and}$$

$$\text{Bias Weight} = w_b(i)' = w_b(i) + 2*u_b*error(i)';$$

where error (i)' is a computed error of the first iteration, $ECG_2(i-1)$ is a reference input at $i-1$, $ECG_1(i)^T$ is a primary input matrix transpose, $w_b(i)$ is the bias weight, W(i)' is a computed weight matrix of the first iteration, W(i) is a starting weight computed in the previous cycle, $u_i$ is a feedback coefficient, $ECG_1(i)$ is a primary input matrix, $w_b(i)'$ is a bias weight for the first iteration, and $u_b$ is a feedback coefficient for modifying the bias weight, 2) a second iteration in said cycle calculates error(i)", W(i)" and $w_b(i)$" as;

$$error(i)'' = ECG_2(i+1) - ECG_1(i)^T * W(i)' - w_b(i)';$$

$$W(i)'' = W(i)' + 2*u_i * error(i)'' * ECG_1(i); \text{ and}$$

$$w_b(i)'' = w_b(i)' + 2*u_b * error(i)'';$$

where error(i)" is a computed error of the second iteration, $ECG_2(i+1)$ is a reference input at $i+1$, W(i)" is a computed weight matrix at the second iteration, and $w_b(i)$" is a bias weight for the second iteration, 3) a filtered output value of an $i^{th}$ point is determined as the product of a matrix transpose of the signal at a point i times the adaptive filter weight matrix at point i plus the bias weight value at point i as follows;

$$ecg_f(i) = ECG_1(i)^T * W(i)'' + W_b(i)'',$$

$$error(i) = ECG_2(i) - ecg_f(i),$$

$$W(i)_{next\ cycle} = W(i)'' + 2*u_i * error(i) * ECG_1(i); \text{ and}$$

$$w_b(i)_{next\ cycle} = w_b(i)'' + 2*u_b * error(i)',$$

where $ecg_f(i)$ is a filtered output, error(i) is the error at input i, $W(i)_{next\ cycle}$ is a weight matrix to use in a first iteration of the next cycle, $w_b(i)_{next\ cycle}$ is a base weight to use in a first iteration of the next cycle.

32. The apparatus of claim 31 wherein the adaptively filtered filter window includes all or a portion of one or more ECG cycles.

33. The apparatus of claim 32 which further comprises a means for detecting a QRS complex and adaptively filtering the filter window which includes a portion of one or more ECG cycles, the portion being about and containing the QRS complex.

34. The apparatus of claim 33 wherein the adaptively filtered filter window is about 400 milliseconds in duration.

35. The apparatus of claim 21 wherein the adaptive filtering within each filter interval includes:
 (a) a means for selecting a last computed value for the bias weight for the filter interval;
 (b) a means for conducting a first updating of both a weight matrix associated with the adaptive filter algorithm and the bias weight for the input signal within the filter interval, using the reference signal for the preceding filter interval;
 (c) a means for conducting a second updating of the weight matrix and the bias weight for the input signal of the filter interval using the reference signal of the subsequent filter interval;
 (d) a means for calculating an output signal by multiplying the second updated weight matrix of the filter interval by the associated input signal, and adding the bias weight;
 (e) a means for conducting a third updating of the weight matrix and bias weight of step (d) associated with the filter interval using the output calculated in step (d), and storing the third updating of the weight matrix and bias weight for use in a subsequent cycle.

36. The apparatus of claim 35 wherein the filter interval is one sample point in duration and the weight matrix is a five element weight matrix.

37. The apparatus of claim 21 wherein the display includes a means for computation of predefined measurements of the patient's electrocardiographic activity either in fully processed individual beats or in averages of selected fully processed beats, wherein the number of beats is selectable.

38. The apparatus of claim 37 wherein the display includes a means for computation of the root mean squared amplitude of the last 40 milliseconds of a QRS complex within the filter interval.

39. The apparatus of claim 37 wherein the display includes a means for computation of the duration of a QRS complex within the filter interval.

40. The apparatus of claim 37 wherein the display includes a means for computation of a low amplitude signal duration.

41. A method of detecting low level biophysical signals of a cyclic nature at the surface of a patient comprising the steps of:
  (a) acquiring two or more biophysical signals at a plurality of external locations on the surface of a patient;
  (b) filtering the surface biophysical signals with a bandpass filter;
  (c) digitizing the acquired biophysical signals by continuous sampling at a rate equal to or greater than the Nyquist rate;
  (d) storing the digitized biophysical signals;
  (e) processing the digitized biophysical signals to reduce low frequency signal components;
  (f) selecting a reference signal with the remaining biophysical signals referred to as input signals and selecting a filter window in a biophysical cycle from one or more of the digitized biophysical input signals and defining filter intervals within said filter window;
  (g) calculating a feedback coefficient $u_i$ associated with an adaptive filter algorithm for each filter interval within a filter window in a cycle of the biophysical signal from one or more of the digitized biophysical input signals;
  (h) initializing a bias weight associated with an adaptive filtering algorithm for each filter interval by computing an initial value for the bias weight associated with the filter interval;
  (i) thereafter adaptively filtering in time-sequenced manner selected filter intervals of the input signals; and
  (j) displaying or storing the results of the adaptive filtering step.

42. An apparatus for detecting low level biophysical signals of a cyclic nature at the surface of a patient comprising:
  (a) means for acquiring two or more biophysical signals at a plurality of external locations on the surface of a patient;
  (b) means for bandpass filtering the surface biophysical signals;
  (c) a means for digitizing the acquired biophysical signals by continuous sampling at a rate equal to or greater than the Nyquist rate;
  (d) a means for storing the digitized biophysical signals;
  (e) a means for processing the digitized biophysical signals to reduce low frequency signal components;
  (f) a means for selecting a reference signal with the remaining biophysical signals referred to as input signals and a means for selecting a filter window in a biophysical cycle from one or more of the digitized biophysical input signals and defining filter intervals within said filter window;
  (g) a means for calculating a feedback coefficient $u_i$ associated with an adaptive filter algorithm for each filter interval within a filter window in a cycle of the biophysical signal from one or more of the digitized biophysical input signals;
  (h) a means for initializing a bias weight associated with an adaptive filtering algorithm for each filter interval by computing an initial value for the bias weight associated with the filter interval;
  (i) a means for thereafter adaptively filtering in time-sequenced manner selected filter intervals of the input signals; and
  (j) a means for displaying or storing the results of the adaptive filtering step.

* * * * *

UNITED STATES PATENT AND TRADEMARK OFFICE
CERTIFICATE OF CORRECTION

PATENT NO. : 5,341,811   Page 1 of 4
DATED : August 30, 1994
INVENTOR(S) : Gerald G. Cano It is certified that error appears in the above-indentified patent and that said Letters Patent is hereby corrected as shown below:

Column 2 Line 67 "potential s" should read --potentials--.

Column 8 Line 6 after "above," insert --the--.

Column 10 Line 4 "HZ" should read --Hz--.

Column 10 Line 17, the paragraph beginning with "increment", insert to the right as a new equation number, --(6)--.

Column 10 Line 55 after "selectable" insert --.--.

Column 11 Line 33 "[w(i-n)" should read --[w(i,-n)--.

Column 11 Line 33 "w(i+n)]$^T$," should read --w(i,+n)]$^T$,--.

Column 11 Line 46 "transpose." should read --transpose;--.

Column 12 Line 42 "ECG$_2$)i-1)" should read --ECG$_2$(i-1)--.

Column 12 Line 45 "+ecg$_2$(i-1)" should read --+ecg$_2$(i+1)--.

Column 12 Line 53 "W(i)'=W(i)'=W(i)" should read --W(i)'=W(i)--.

UNITED STATES PATENT AND TRADEMARK OFFICE
CERTIFICATE OF CORRECTION

PATENT NO. : 5,341,811

DATED : August 30, 1994

INVENTOR(S) : Gerald G. Cano

It is certified that error appears in the above-indentified patent and that said Letters Patent is hereby corrected as shown below:

Column 13 Line 68 "[$ecg_f(i)$beat k]" should read --[$ecg_f(i)_{beat\ k}$]--.

Column 14 Line 15, the paragraph beginning with "W(i)' ", insert to the right as a new equation number, --(31)--.

Claim 1 Line 53 Column 16 "step" should read --steps--.

Claim 8 1) Line 38 Column 17 "$f_s$+pi/2), and" should read --$f_s$) and--.

Claim 9 Line 2 Column 18 "$u_i\ \beta$" should read --$u_i = \beta$--.

Claim 10 Lines 12-13 Column 18 "[$ecg_f(i)_{beat\ j}$[" should read --[$ecg_f(i)_{beat\ j}$]--.

Claim 11 Line 41 Column 18 "tranpose," should read --transpose,--.

Claim 11 Line 54 Column 18 "$u_i$error(i)'' " should read --$u_i$*error(i)''--.

Claim 11 Line 57 Column 18 "error*(i)'' " should read --error(i)''--.

Claim 11 Line 57 Column 18 "compound" should read --computed--.

Claim 11 Line 63 Column 18 "produce" should read --product--.

UNITED STATES PATENT AND TRADEMARK OFFICE
CERTIFICATE OF CORRECTION

PATENT NO. : 5,341,811
DATED : August 30, 1994
INVENTOR(S) : Gerald G. Cano

It is certified that error appears in the above-indentified patent and that said Letters Patent is hereby corrected as shown below:

Claim 11 Line 11 Column 19 "the first" should read --a first--.

Claim 19 Line 60 Column 19 before "QRS" insert --a--.

Claim 21 Line 1 Column 20 after "(b)" insert --a means for bandpass filtering the surface ECG signals;--.

Claim 21 Line 1 Column 20 before "means" insert as the beginning of a new paragraph --(c) a--.

Claim 21 Line 2 Column 20 "grater" should read --greater--.

Claim 21 Line 7 Column 20 before "means" insert --a--.

Claim 21 Line 20 Column 20 "a initial" should read --an initial--.

Claim 28 Line 67 Column 20
"$w_{cosine\ next} = w_{cosine\ next} = w_{cosine}$" should read
--$w_{cosine\ next} = w_{cosine}$--.

Claim 28 Line 1 Column 21, the paragraph beginning with "increment", insert to the right as a new equation number, --(6)--.

Claim 29 Line 23 Column 21 "$\sigma noise$" should read --$\sigma_{noise}$--.

UNITED STATES PATENT AND TRADEMARK OFFICE
CERTIFICATE OF CORRECTION

PATENT NO. : 5,341,811
DATED : August 30, 1994
INVENTOR(S) : Gerald G. Cano

It is certified that error appears in the above-indentified patent and that said Letters Patent is hereby corrected as shown below:

Claim 30 Line 41 Column 21 "$w_b I$" should read --$w_b i$--

Claim 31 Line 49 Column 21 "where" should read --wherein--.

Claim 31 Line 51 Column 21 before "a first" insert --1)--.

Claim 31 Line 54 Column 21 after "*" insert --W(i)- --.

Claim 31 Line 56 Column 21 "error(i); and" should read --error(i)'*$ECG_1$(i); and--.

Claim 31 Line 32 Column 22 "base" should read --bias--.

Claim 42 Line 13 Column 24 before "means" insert --a--.

Claim 42 Line 16 Column 24 before "means" insert --a--.

Signed and Sealed this

Twenty-first Day of February, 1995

Attest:

BRUCE LEHMAN

Attesting Officer  Commissioner of Patents and Trademarks